(12) United States Patent
Pochy

(10) Patent No.: US 7,880,874 B2
(45) Date of Patent: Feb. 1, 2011

(54) SURFACE PARTICLE COUNTER

(75) Inventor: Rocco Pochy, Fremont, CA (US)

(73) Assignee: Lighthouse Worldwide Solutions, Inc., Fremont, CA (US)

( * ) Notice: Subject to any disclaimer, the term of this patent is extended or adjusted under 35 U.S.C. 154(b) by 54 days.

(21) Appl. No.: 12/196,123

(22) Filed: Aug. 21, 2008

(65) Prior Publication Data

US 2009/0051908 A1    Feb. 26, 2009

Related U.S. Application Data

(60) Provisional application No. 60/957,123, filed on Aug. 21, 2007.

(51) Int. Cl.
*G01N 21/84* (2006.01)
*G01N 21/00* (2006.01)

(52) U.S. Cl. ................. 356/237.2; 356/335; 73/864.33; 73/864.71

(58) Field of Classification Search ......... 356/432–437, 356/335–343, 440; 73/864.33, 864.71, 864.34, 73/864.81, 863.23, 863.25
See application file for complete search history.

(56) References Cited

U.S. PATENT DOCUMENTS

| 4,130,754 | A | * | 12/1978 | Fosslien | 377/12 |
| 5,253,538 | A | * | 10/1993 | Swick et al. | 73/864.34 |
| 5,949,001 | A | * | 9/1999 | Willeke | 73/865.5 |
| 5,974,868 | A | * | 11/1999 | Decain et al. | 73/61.72 |
| 6,639,670 | B2 | * | 10/2003 | Carpenter | 356/335 |
| 7,010,991 | B2 | * | 3/2006 | Lutz et al. | 73/864.33 |

* cited by examiner

*Primary Examiner*—Sang Nguyen
(74) *Attorney, Agent, or Firm*—Michael L. Greenberg, Esq.; Greenberg & Lieberman, LLC

(57) ABSTRACT

A surface particle-counting device where the scanner element and the particle counting element have been combined so to reduce the number of lost particles and increase the overall efficiency of the particle-counting device. By removing the conventional tube that connects the scanner element and the particle counting element accuracy is increased.

9 Claims, 2 Drawing Sheets

SURFACE PARTICLE COUNTER

This is a non-provisional application claiming priority to provisional patent application No. 60/957,123 filed on Aug. 21, 2007.

FIELD OF THE INVENTION

The present invention relates to a scanner that is combined with a particle sensor for an improved and more efficient surface particle-counting device.

BACKGROUND OF THE INVENTION

Surface particle counters typically operate by using a scanner head that moves over the surface of the area of interest, pulling particles into the flow through a conduit. This conduit transports the particles to a counter. After being counted in the counter, the airflow is filtered and reutilized providing a stream of air in the scanner head meant to disturb the particles on the surface.

Typically, prior inventions have a conduit separates the scanner and counter. Therefore, the typical process for a particle-counting device involves particles passing through a scanner where the particles are then pulled and transferred through a conduit before being counted at the counter. After being counted, the particles are then moved by the fluid stream generated by the particle-counting device through a pump and then a filter, ultimately ending up back at the scanner where the particles are pulled again. This is shown in FIG. 1.

As we see in FIG. 1, a conventional scanner (1) is positioned close to a conventional surface (2). Blowing air (3) exits conventional scanner (1) and disburses particles from conventional surface (2) so that the particles are sucked through conventional scanner (1) through first tube (4) and into conventional housing (105). Conventional particle counter (6) receives the sucked particles from first tube (4) and counts the particles. The particles then travel to conventional pump (7) where some particles exit conventional housing (105); whereas other particles move from the conventional pump (7) to conventional filter (8). Most particles are trapped conventional filter (8) but the air in which they were traveling moves through second tube (9) and returns to conventional scanner (1) as blowing air (3).

One of the problems with this mechanism is the transport of particles from the surface to the particle counter. Because of the distance between the surface of interest and the particle sensor, there are particle transport issues that may result in loss of particles in such problematic manners as particles sticking to the transport tube and particle traps caused by gaps and dead space of the various fittings. This results in inaccurate readings from the particle counter. This problem becomes greater as the particle size increases. The present invention addresses this issue by combining the scanner element and the particle sensor into one apparatus. In this way, the present invention saves one significant step in the particle flow process. By effectively shortening the distance that particles must travel, the present invention fixes an important problem by avoiding the potential loss of particles before being counted.

U.S. Pat. No. 5,253,538 refers to a particle counting device comprising a scanner and a particle counter, however, the particles must first pass through the scanner and then a "plurality of tubes" before reaching the particle counter. This setup allows many places for particles to stick to before reaching the counter. The present invention aims to solve this problem by placing the particle counter directly near the scanner so that the particles do not have to pass through a plurality of tubes before being counted.

SUMMARY OF THE INVENTION

The present invention combines a scanner and a particle sensor or counter into varying types of particle-counting devices. The present invention eliminates a number of steps in the typical process. Because the present invention features a scanner combined with a counter, the overall efficiency of the particle-counting device is vastly improved. This is because combining the two elements together into the present invention eliminates particle traps and particle loss due to transport from the scanner to counter.

The present invention has both a scanner and counter elements. The scanner features a head that when placed near a surface has inlets that draw particles to the particle-sensing element. The scanner also contains a channel used to draw air near the surface to avoid creating a vacuum between the scanner and the surface. The stream of air flows from around the scanner, across the surface, and then into the particle counter.

The particle counter consists of a light source to illuminate particles as they pass through the view volume and a light detector to register the scattered light off the particles as they pass through (Light Scattering Design), or to attenuate the light as the particles pass between the light source and light detect (Light Blocking Design). Once the particles have been counted, there is a tube to a vacuum source to assure that a constant flow is maintained and to exhaust the air stream.

DETAILED DESCRIPTION OF THE PREFERRED EMBODIMENT

Figure 1:
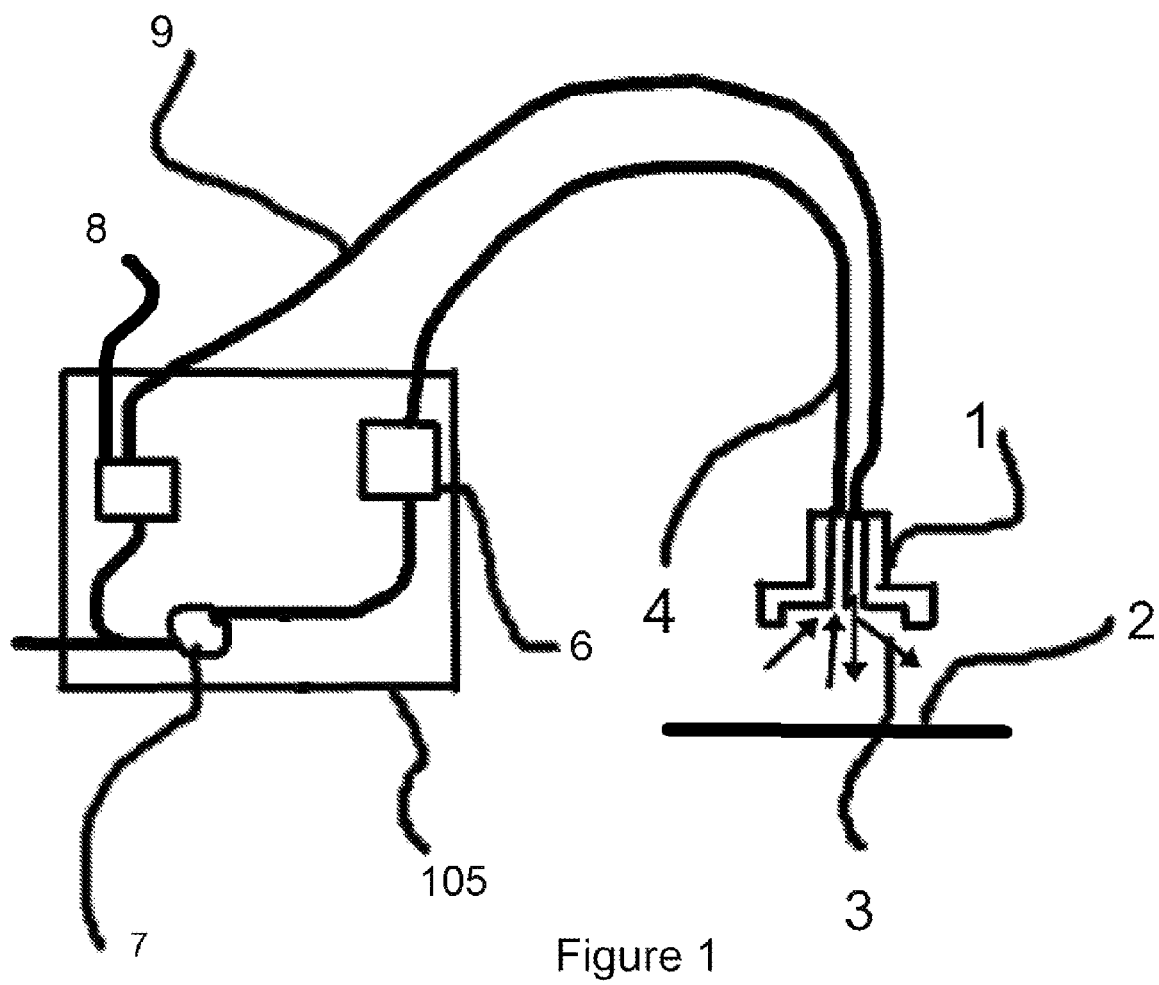
FIG. 1 shows a schematic of prior art of the present invention.
Figure 2:
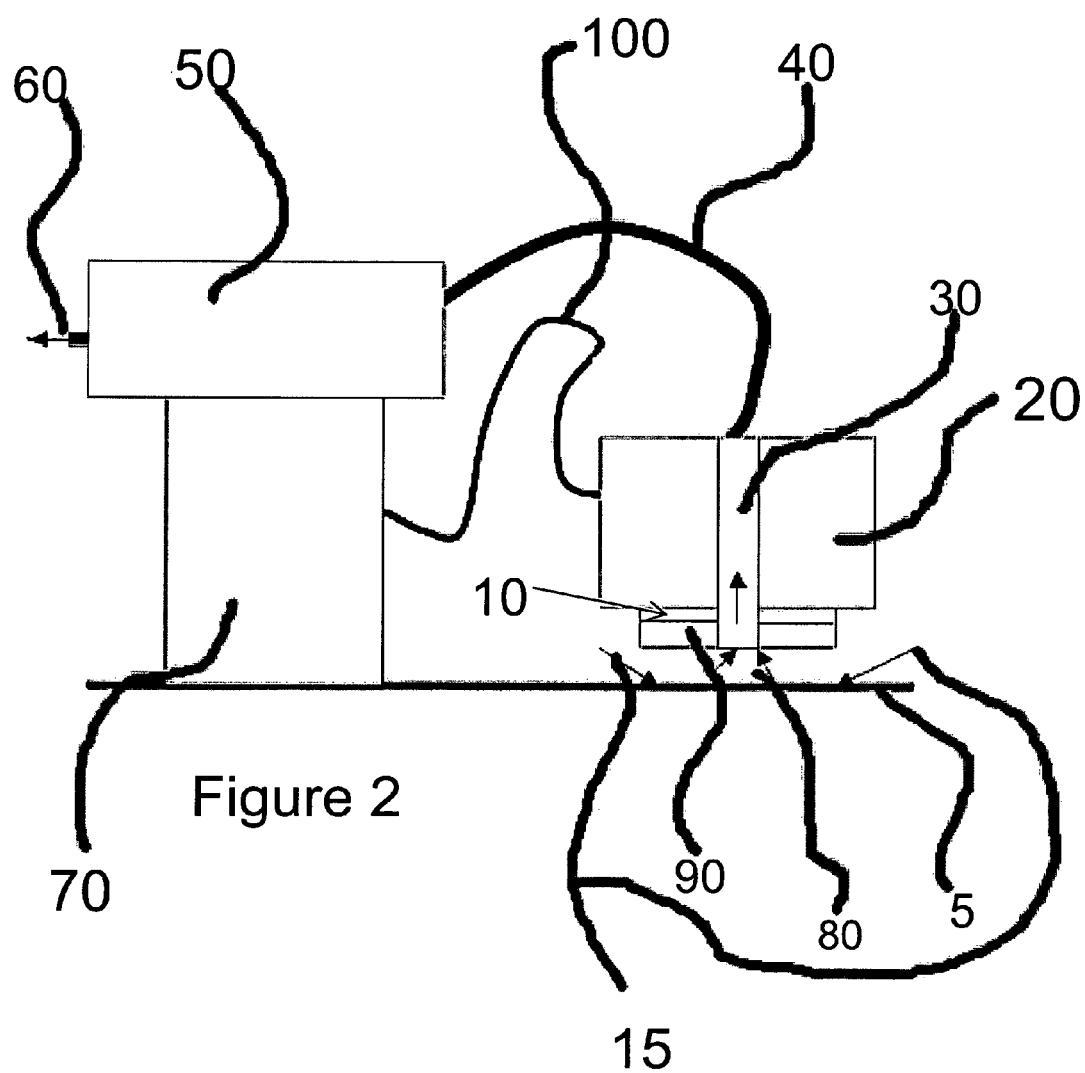
FIG. 2 shows a block diagram of the present invention.

In FIG. 2, we see an environmental view of the present invention. In this view, we see that the scanner (10) is attached to the particle sensor (20). With the particle conduit (30) burrowed in between the scanner (10) and the particle sensor (20), both elements can remain attached surrounding the particle conduit (30) while eliminating particle traps and other elements that would otherwise cause particles to be lost during transfer.

In FIG. 2, we see that the scanner (10) and the particle sensor (20) are raised slightly above the surface (5). When the present invention is activated, the stream of airflow (15) will pass through the channel (80) that effectively separates the scanner (10) and particle sensor (20) from the surface (5). The channel (80) draws air from near the surface (5) in order to help avoid the problem of creating a vacuum between the scanner (10) and the surface (5).

Filters contained in the scanner head (90) operate to filter out the external air before the particles enter the scanner (10). The stream of airflow (15) will then be sucked from the channel (5) where the particles have been concentrated and forced into the particle conduit (30). The particle conduit (30) serves to pass the stream of airflow (15) through the scanner (10) and the particle sensor (20).

FIG. 2 also shows us that the stream of airflow (15) is made possible to be forced through the present invention through the use of the vacuum source (50). When the present invention is powered on, the vacuum source (50) effectively uses the power to suck particles through the created stream of airflow (15). The vacuum source (50) is connected to the particle conduit (30) through the use of vacuum tubing (40). The vacuum tubing (40) is a tube that permits air to pass through in a powerful manner based on the power emanating from the vacuum source (50). The vacuum source (50) and its related vacuum tubing (40) are also important because they help maintain a constant flow after the particles have been counted.

Once the particles are sucked through the combined scanner (10) and particle sensor (20) and their related elements, we see from FIG. 2 that the particles may then be sucked through the vacuum tubing (40) and into the vacuum source (50). The vacuum source (50) includes an exhaust element (60) that serves to vacate the stream of airflow (15) and all particles remaining. It is important to note that the exhaust element (60) is not reconnected to the present invention. This means that the exhaust from the pump contained in the vacuum source is not recycled to be again included into the particle capturing system of the present invention.

Another aspect of the present invention as seen in FIG. 2 is the particle counter electronics (70). The particle counter electronics (70) operates in communication with the scanner (10). This process is conducted via the use of a power and signal line (100). The power and signal line (100) is dual in nature being that it provides actual power to the scanner (10) and also calculates and emits the proper signals to the scanner (10).

In one embodiment of the present invention, air is filtered in the scanner head (90) prior to entering the particle counter. Unlike conventional systems that filter air after particles have been counted, prior to returning the air to the scanner head (90) the present invention preferably filters air not to prevent contamination upon reintroduction of air to the surface (5) being scanned but rather to increase the efficacy of the particle counter.

It should be understood that all numbered parts of the present invention are of conventional nature and design.

I claim:

1. A method for counting particles, comprising:
    attaching a scanner to a particle sensor such that a particle conduit is completely surrounded by the scanner and the particle sensor but for a first opening where air enters the particle conduit and a second opening where air exists the particle conduit;
    raising the scanner and the particle sensor slightly above a surface;
    passing a stream of airflow through a channel;
    filtering out external air before particles enter the scanner via a scanner head;
    sucking the stream of airflow from the channel, whereby concentrated particles are forced into the particle conduit;
    forcing the stream of airflow through the use of a vacuum source, the vacuum source powered to suck particles through a created stream of airflow;
    maintaining a constant flow after particles have been counted via the vacuum source and a vacuum tubing;
    vacating the stream of airflow and all remaining particles through the use of an exhaust element; and
    providing power to the scanner via a power and signal line, the power and signal line also serving to calculate and emit signals to the scanner.

2. The method for counting particles of claim 1, further comprising operating particle counter electronics in communication with the scanner.

3. The method for counting particles of claim 1, further comprising connecting the vacuum source to the particle conduit through use of the vacuum tubing.

4. The method for counting particles of claim 1, further comprising locating filters in a scanner head.

5. The method for counting particles of claim 1, further comprising passing the stream of airflow through the scanner and particle sensor via the particle conduit.

6. The method for counting particles of claim 1, further comprising connecting an exhaust element to the vacuum source.

7. The method for counting particles of claim 1, further comprising housing together the scanner and the particle counter such that particles are conducted between the scanner and the particle sensor without the use of the particle conduit.

8. A method for counting particles, comprising:
    attaching a scanner to a particle sensor such that a particle conduit is completely surrounded by the scanner and the particle sensor but for a first opening where air enters the particle conduit and a second opening where air exists the particle conduit;
    raising the scanner and the particle sensor slightly above a surface;
    passing a stream of airflow through a channel;
    filtering out external air before particles enter the scanner via a scanner head;
    sucking the stream of airflow from the channel, whereby concentrated particles are forced into the particle conduit;
    forcing the stream of airflow through the use of a vacuum source, the vacuum source powered to suck particles through a created stream of airflow;
    maintaining a constant flow after particles have been counted via the vacuum source and a vacuum tubing;
    vacating the stream of airflow and all remaining particles through the use of an exhaust element;
    providing power to the scanner via a power and signal line, the power and signal line also serving to calculate and emit signals to the scanner;
    operating particle counter electronics in communication with the scanner;
    connecting the vacuum source to the particle conduit through use of the vacuum tubing;
    locating filters in a scanner head;
    passing the stream of airflow through the scanner and particle sensor via the particle conduit; and
    connecting an exhaust element to the vacuum source.

9. A particle counter, comprising:
    a scanner connected to a particle sensor;
    a particle conduit completely surrounded by the scanner and the particle sensor but for a first opening where air enters the particle conduit and a second opening where air exists the particle conduit;
    said scanner and said particle sensor positioned slightly above a surface;
    a channel positioned between said scanner and said particle sensor, said channel formed to allow a stream of airflow to pass through;
    said channel positioned to draw air from near said surface to avoid the creation of a vacuum between said scanner and said surface;
    a filter contained within a scanner head, said filter formed to filter out external air before particles enter said scanner;
    said particle conduit formed to pass said stream of airflow through said scanner and said particle sensor;
    a vacuum source, said vacuum source connected to said particle conduit via vacuum tubing;
    an exhaust element included with said vacuum source; and
    particle counter electronics in communication with said scanner.

* * * * *